United States Patent
Huang

(10) Patent No.: US 10,550,147 B2
(45) Date of Patent: Feb. 4, 2020

(54) CYCLOPENTANOPERHYDRO-PHENANTHRENE FRAMEWORK COMPOUNDS AND PREPARATION METHOD THEREFOR

(71) Applicant: SICHUAN JINGHUACHUANG BIOTECHNOLOGY CORPORATION, Sichuan (CN)

(72) Inventor: Wen Huang, Sichuan (CN)

(73) Assignee: SICHUAN JINGHUACHUANG BIOTECHNOLOGY CORPORATION, Sichuan (CN)

( * ) Notice: Subject to any disclaimer, the term of this patent is extended or adjusted under 35 U.S.C. 154(b) by 0 days.

(21) Appl. No.: 15/304,424

(22) PCT Filed: Jan. 8, 2015

(86) PCT No.: PCT/CN2015/070372
§ 371 (c)(1),
(2) Date: Jan. 19, 2017

(87) PCT Pub. No.: WO2015/158163
PCT Pub. Date: Oct. 22, 2015

(65) Prior Publication Data
US 2017/0190733 A1    Jul. 6, 2017

(30) Foreign Application Priority Data

Apr. 14, 2014   (CN) .......................... 2014 1 0146063

(51) Int. Cl.
*C07J 71/00* (2006.01)
*C07J 43/00* (2006.01)
*C07J 53/00* (2006.01)

(52) U.S. Cl.
CPC ......... *C07J 71/0031* (2013.01); *C07J 43/003* (2013.01); *C07J 53/002* (2013.01); *C07J 71/0005* (2013.01)

(58) Field of Classification Search
None
See application file for complete search history.

(56) References Cited

U.S. PATENT DOCUMENTS 2,716,116 A * 8/1955 Fontaine .................. C07J 71/00
540/17
2008/0287662 A1* 11/2008 Wiesman ................. C07J 71/00
536/4.1

FOREIGN PATENT DOCUMENTS

| CN | 1652794 | 8/2005 |
| CN | 1821260 | 8/2006 |
| FR | 2743561 | 7/1997 |
| GB | 843664 | 8/1960 |
| WO | WO2003/077869 | 9/2003 |

OTHER PUBLICATIONS

Chyhyrynets et al. Materials Science, vol. 49, No. 3, Nov. 2013.*
Lee at al. Journal of the American Chemical Society (1976), 98(6), 1634-5.*
Tomkiel et al, "Electrochemical synthesis of glyconjugates of 3β-hydr4oxy-Δ5-steroids by using non-activated sugars and steroidal thioethers," Tetrahedron, 69:8904-8913 (2013).
Fu et al, "Synthesis of diosgenin derivatives and their antithrombotic activity," Drugs & Clinic, 26(1):46-49 (2011).
Zheng et al, "The design and synthesis of diosgenin anti-tumor derivatives (III)," West China Journal Pharmaceutical Sciences, 26(2):107-111 (Feb. 2011).
Zhang et al, "Study on the synthesis and antitumor activities of diosgenyl saponin derivaties," West China Journal Pharmaceutical Sciences, 28(3):229-231 (Mar. 2013).
PCT International Preliminary Report on Patentability for PCT/CN2015/070372 (6 pages) (English Translation).
PCT International Search Report for PCT/CN2015/070372 (6 pages).

* cited by examiner

*Primary Examiner* — Ana Z Muresan
(74) *Attorney, Agent, or Firm* — Edward D. Grieff; Mintz, Levin, Cohn, Ferris, Glovsky and Popeo, P.C.

(57) ABSTRACT

The present invention pertains to the field of pharmaceutical chemistry, and relates to compounds having cyclopentanoperhydrophenanthrene skeletons and preparation methods therefore. The compounds have some physiological activity, and are useful as synthons/intermediates for further synthesizing some compounds having specific structures. These compounds and salts thereof are useful as lead compounds for synthesizing pharmaceuticals, pesticides and new materials. From this, further screen and preparation by chemical, biological and medical means offer new compounds that are more valuable and have important applications, achieving the object of inventing and creating new drugs.

3 Claims, No Drawings

US 10,550,147 B2

CYCLOPENTANOPERHYDRO-PHENANTHRENE FRAMEWORK COMPOUNDS AND PREPARATION METHOD THEREFOR

TECHNICAL FIELD OF THE INVENTION

The present invention relates to compounds having cyclopentanoperhydrophenanthrene skeletons and preparation methods therefore. The compounds may have some physiological activity, and are useful as synthons/intermediates for further synthesizing some compounds having specific structures.

BACKGROUND OF THE INVENTION

Cyclopentanoperhydrophenanthrene compounds exist widely in plants and animals, and play an important role in their life processes. Biologically active cyclopentanoperhydrophenanthrene compounds have long been a hot research area, and nowadays these compounds still play an important role in community, offering great social and economic benefits.

In pharmaceutical chemistry, natural endogenous compounds from plants and animals are studied in order to find physiologically active and effective ingredients as well as lead compounds for synthesizing pharmaceuticals, pesticides and new materials. From this, further screen and preparation by chemical, biological and medical means offer new compounds that are more valuable and have important applications, achieving the object of inventing and creating new drugs. In order to enrich compound libraries, reveal biological relations of compounds, and provide new skeletons and new lead compounds for the screen of active compounds, we synthesized compounds having cyclopentanoperhydrophenanthrene skeletons that are substituted or unsubstituted, with or without heterocyclic structures.

SUMMARY OF THE INVENTION

The present invention aims at enriching compound libraries, revealing biological relations of compounds, and providing new skeletons for the screen of active compounds, and thereby provides compounds having cyclopentanoperhydrophenanthrene skeletons that are substituted or unsubstituted, with or without heterocyclic structures.

The present invention provides compounds represented by the following formula:

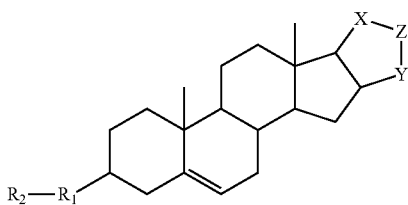

or pharmaceutically acceptable salts thereof,
wherein
$R_1$ is O, N, S or $C_1$-$C_8$ hydrocarbyl;
$R_2$ is $CH_3CO$, $C_6H_5CO$, $R_3NH(CH_2)_nCO$, $R_5NHCH(R_4)CO$, sulfonyl, diethoxyphosphonate, 2-[bis(pivaloyloxy)methoxy]phosphonomethoxyethyl, 3,4,5-trihydroxybenzoyl, 3-(3,4-dihydroxyphenyl)-2-acryloyl, 1,3,4,5-tetrahydroxy-1-cyclohexylformyl, glucosyl, galactosyl, ribosyl, deoxyribosyl, rhamnosyl, arabinosyl, lactosyl, xylosyl, or a group according to the formula $-A_1A_2$, $-A_1OA_2$, $-A_1OC(O)A_2$, $-A_1C(O)OA_2$, $-A_1NHA_2$, $-A_1NHCOA_2$ or $-A_1NHCOA_2$;
X is H, N, O or $C_1$-$C_8$ hydrocarbyl;
Y is a halogen, N, O or S substituted or unsubstituted $C_1$-$C_8$ hydrocarbyl group or heterocyclic group; and
Z is a saturated or unsaturated $C_1$-$C_{18}$ hydrocarbyl group, $R_3NH(CH_2)_nCO$, $R_5NHCH(R_4)CO$, glucosyl, galactosyl, ribosyl, deoxyribosyl, rhamnosyl, arabinosyl, lactosyl, cellobiosyl, xylosyl, or a group according to the formula $-A_1A_2$, $-A_1OA_2$, $-A_1OC(O)A_2$, $-A_1C(O)OA_2$, $-A_1NHA_2$, $-A_1NHCOA_2$ or $-A_1NHCOA_2$;
wherein $R_3$ and $R_5$ are H, $CH_3CO$, $C_6H_5CO$, sulfonyl, diethoxyphosphonate, a saturated or unsaturated $C_1$-$C_{18}$ hydrocarbyl group or a heterocyclic group; $R_4$ is a saturated or unsaturated $C_1$-$C_{18}$ hydrocarbyl group or a heterocyclic group; Z may be absent, or may be a group connecting X and Y to form a ring; and $A_1$ and $A_2$ are hydrogen, $C_1$-$C_{18}$ alkyl, halogen substituted $C_1$-$C_{18}$ alkyl, $C_3$-$C_{12}$ heterocyclyl, a $C_1$-$C_{18}$ aliphatic acid group, or a $C_1$-$C_{18}$ alkyl or aliphatic acid group substituted by an oxygen, sulfur or nitrogen atom.

In particular, provided are compounds represented by the following formula:

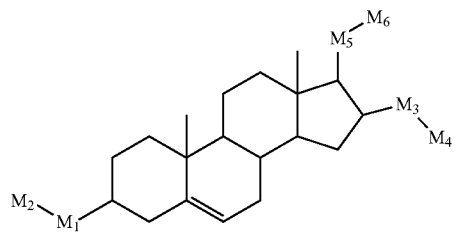

or pharmaceutically acceptable salts thereof,
wherein
$M_1$, $M_3$ and $M_5$ are O, N, S or $C_1$-$C_8$ hydrocarbyl; and
$M_2$, $M_4$ and $M_6$ are $CH_3CO$, $C_6H_5CO$, $R_3NH(CH_2)_nCO$, $R_5NHCH(R_4)CO$, sulfonyl, diethoxyphosphonate, 2-[bis(pivaloyloxy)methoxy]phosphonomethoxyethyl, 3,4,5-trihydroxybenzoyl, 3-(3,4-dihydroxyphenyl)-2-acryloyl, 1,3,4,5-tetrahydroxy-1-cyclohexylformyl, glucosyl, galactosyl, ribosyl, deoxyribosyl, rhamnosyl, arabinosyl, lactosyl, or a group according to the formula $-A_1A_2$ wherein $A_1$ and $A_2$ are hydrogen, a substituted or unsubstituted $C_1$-$C_{18}$ hydrocarbyl group, $C_3$-$C_{12}$ heterocyclyl, a substituted or unsubstituted $C_1$-$C_{18}$ aliphatic acid group, or a $C_1$-$C_{18}$ alkyl or aliphatic acid group substituted by $C_3$-$C_{12}$ heterocyclyl.

In particular, provided are compounds represented by the following formula:

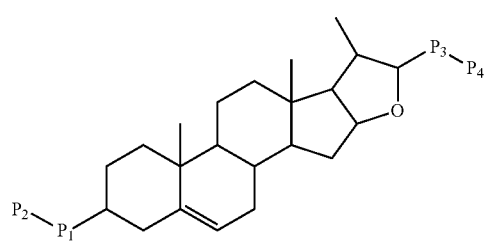

or pharmaceutically acceptable salts thereof, wherein
P$_1$ and P$_3$ are O, N, S or C$_1$-C$_8$ hydrocarbyl; and
P$_2$ and P$_4$ are CH$_3$CO, C$_6$H$_5$CO, R$_3$NH(CH$_2$)CO, R$_5$NHCH(R$_4$)CO, sulfonyl, diethoxyphosphonate, 2-[bis(pivaloyloxy)methoxy]phosphonomethoxyethyl, glucosyl, galactosyl, ribosyl, deoxyribosyl, rhamnosyl, arabinosyl, lactosyl, or a group according to the formula -A$_1$A$_2$ wherein A$_1$ and A$_2$ are hydrogen, a substituted or unsubstituted C$_1$-C$_{18}$ hydrocarbyl group, C$_3$-C$_{12}$ heterocyclyl, a substituted or unsubstituted C$_1$-C$_{18}$ aliphatic acid group, or a C$_1$-C$_{18}$ alkyl or aliphatic acid group substituted by C$_3$-C$_{12}$ heterocyclyl.

In particular, provided are compounds represented by following formula:

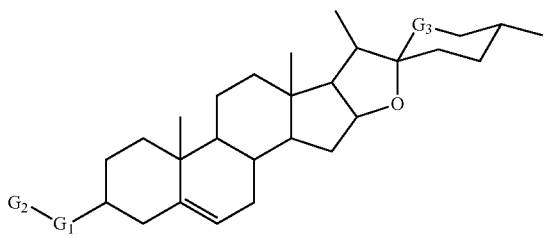

or pharmaceutically acceptable salts thereof,
wherein
G$_1$ is C, O, S or N;
G$_2$ is a substituted or unsubstituted C$_1$-C$_{18}$ hydrocarbyl group, C$_3$-C$_{12}$ heterocyclyl, a substituted or unsubstituted C$_1$-C$_B$ aliphatic acid group, a C$_1$-C$_{18}$ alkyl or aliphatic acid group substituted by C$_3$-C$_{12}$ heterocyclyl, or a group according to the formula -A$_1$A$_2$ wherein A$_1$ and A$_2$ are hydrogen, a substituted or unsubstituted C$_1$-C$_{18}$ hydrocarbyl group, C$_3$-C$_{12}$ heterocyclyl, a substituted or unsubstituted C$_1$-C$_{18}$ aliphatic acid group, or a C$_1$-C$_B$ alkyl or aliphatic acid group substituted by C$_3$-C$_{12}$ heterocyclyl; and
G$_3$ is C, O, S or N.

The term "hydrocarbyl" used herein means a saturated or unsaturated aliphatic hydrocarbon, which can be a linear, branched or cyclic alkane.

The term "heterocyclyl" refers to a 3- to 12-membered heterocyclic group having a ring in which one, two, three or four carbon atoms are replaced by oxygen, nitrogen and/or sulfur atoms. Heterocyclyl is, for example, pyrrolyl, thienyl, imidazolyl, thiazolyl, piperazinyl, pyridazinyl, benzopyrrolyl or tetraazacyclododecyl, but is not limited to these groups.

In particular, provided are the following compounds:
(25R)-3β-N-(6-aminohexamide)-spirost-5-ene (4)
(25R)-3β-N-(4-acetoxy-phenyl-1-amino)-spirost-5-ene (5)
(25R)-3β-S-(6-aminohexanethioate)-spirost-5-ene (7)
(25R)-3β-N-(2-(tert-butoxycarbonyl)-amino-6-N-aminohexanoic acid methyl ester)-spirost-5-ene (8)
(25R)-3β-N-(2-propyn-amino-6-N-aminohexanoic acid methyl ester)-spirost-5-ene (9)
(25S)-3β-N-(2-propyn-amino-6-N-aminohexanoic acid methyl ester)-furost-5-en-26-ol (10)
(25S)-3β-N-(2-propyn-amino-6-N-aminohexanoic acid methyl ester)-26-O-(2,3,5-tri-O-acetyl-β-D-ribofuranosyl)-furost-5-ene (11)
(25S)-3β-N-(2-propyn-amino-6-N-aminohexanoic acid)-26-O-(2,3,5-tri-O-acetyl-β-D-ribofuranosyl)-furost-5-ene (12)
(25S)-furost-5-en-3β,26-di-O-(6-aminohexanoate) (13)
(25S)-3β-N-(6-aminohexanoic acid)-26-O-(3-deoxy-β-D-ribofuranosyl)-furost-5-ene (14)
(25R)-3-O-benzyl-26-O-(tert-butyldimethylsilyl)-cholest-5-en-16β-ol (15)
(25R)-3-O-benzyl-16-O-(2,3,5-tri-O-acetyl-β-D-ribofuranosyl)-cholest-5-en-26-ol (17)
(25R)-3-O-benzyl-16-O-(2,3,5-tri-O-acetyl-β-D-ribofuranosyl)-26-(4-O-7-nitro-1,2,3-benzoxadiazol)-cholest-5-ene (18)
(25R)-16-O-(2,3,5-tri-O-acetyl-β-D-ribofuranosyl)-26-(4-O-7-nitro-1,2,3-benzoxadiazol)-cholest-5-en-3-ol (19)
(25R)-16-O-(2,3,5-tri-O-acetyl-β-D-ribofuranosyl)-26-(4-O-7-nitro-1,2,3-benzoxadiazol)-cholest-5-en-3-O-yl 2,6-diaminohexanoate (20).

The invention is further described in detail below by way of examples. However, this should not be construed as that the subject matter of the invention is limited to the following examples. Any technique implemented based on the invention is within the scope of the present invention.

DETAILED DESCRIPTION OF THE INVENTION

Example 1

Preparation of (25R)-3β-N-(6-aminohexamide)-spirost-5-ene (4)

Compound 1—(25R)-spirost-5-en-3β-ol (0.42 g, 1 mmol) (Aladdin Reagent Co.) and pyridinium chlorochromate (1.3 g, 6 mmol) were dissolved in anhydrous dichloromethane (25 ml), and were stirred at ambient temperature for 2 h. The reaction was monitored by TLC with a silica gel plate, and when the reaction was completed, an excess amount of dichloromethane was added. The reaction mixture was vacuum filtrated (using a Buchner funnel prefilled with about 3 cm of Celite). The solvent was then removed under vacuum, and the residue was separated with a silica gel column using a mobile phase of petroleum ether:ethyl acetate=2:1, to give Compound 2—(25R)-spirost-5-en-3β-one (0.36 g, 88% yield) as a white powder.

Compound 2 (0.2 g, 0.5 mmol), sodium cyanoborohydride (0.1 g, 1.59 mmol) and aminocaproic acid (0.20 g, 1.5 mmol) were dissolved in 100 ml of anhydrous methanol, and stirred for 1 h, to give Compound 4 (0.21 g, 41%).

$^1$H NMR (400 MHz, CDCl$_3$) δ 5.42 (s, 2H), 5.27 (s, 1H), 4.13 (s, 2H), 3.83 (s, 1H), 3.52 (s, 2H), 3.22 (s, 2H), 2.64 (s, 2H), 2.18 (d, J=0.8 Hz, 2H), 2.08 (s, 2H), 2.07 (s, 5H), 1.95 (s, 1H), 1.87 (d, J=5.4 Hz, 3H), 1.82 (s, 1H), 1.66 (dd, J=20.0, 5.0 Hz, 6H), 1.61-1.47 (m, 18H), 1.43 (s, 2H), 1.36-1.22 (m, 14H), 1.20 (s, 1H), 1.10 (s, 4H), 0.92 (s, 6H), 0.91 (s, 6H), 0.87 (s, 6H), 0.81 (s, 6H), 0.75 (s, 1H). (M+H$^+$)=527.4135.

Compound 5 was obtained using Compound 2 andp-acetoxy aniline as starting materials.

(25R)-3β-N-(4-acetoxy-phenyl-1-amino)-spirost-5-ene (5)

$^1$H NMR (400 MHz, CDCl$_3$) δ 7.01 (s, 15H), 6.78 (s, 15H), 5.28 (s, 4H), 3.65 (s, 8H), 3.53 (s, 10H), 3.34 (s, 3H), 3.27 (s, 4H), 2.63 (s, 7H), 2.26 (s, 22H), 2.17 (s, 3H), 2.11 (s, 5H), 2.08 (s, 4H), 1.96 (s, 6H), 1.87 (d, J=3.3 Hz, 10H), 1.85 (s, 11H), 1.72 (d, J=13.7 Hz, 11H), 1.66-1.52 (m, 56H), 1.48 (d, J=14.8 Hz, 10H), 1.32 (t, J=12.8 Hz, 21H), 1.21 (s, 3H), 0.91 (d, J=20.0 Hz, 45H), 0.99-0.75 (m, 97H). (M+H$^+$)=548.3663.

Example 2

Preparation of (25R)-3β-S-(6-aminohexanethioate)-spirost-5-ene (7)

Compound 1 (0.42 g, 1 mmol), dimethylamino thiocarbamoyl chloride (0.62 g, 5.0 mmol) and sodium hydride (0.12 g, 10 mmol) were dissolved in 25 ml of anhydrous N,N-dimethylformamide, and were stirred at room temperature for 2 h. The temperature was then raised to 250° C., and reaction was continued for 12 h. The reaction was monitored by TLC. When the reaction was completed, solvent was removed under vacuum, and the residue was re-dissolved in methanol. Lithium aluminum hydride (0.12 g, 3.0 mmol) was added, and reaction proceeded at room temperature for 2 h. Dilute hydrochloric acid was added to adjust the pH to 2-3, and reaction proceeded overnight. When the reaction was completed, solvent was removed under vacuum, and the residue was separated with a silica gel column using a mobile phase of dichloromethane:methanol=8:1, to give Compound 6—(25R)-spirost-5-en-3β-thiol (0.378 g, 88% yield).

Compound 6 (0.22 g, 0.5 mmol), Boc-aminocaproic acid (0.35 g, 1.5 mmol), dicyclohexyl carbodiimide (0.52 g, 2.5 mmol) and N,N-dimethylpyridine (24 mg, 0.2 mmol) were dissolved in 10 ml of anhydrous dichloromethane, and reaction proceeded at room temperature for 4 h. The reaction mixture was filtrated, and 0.5 ml of trifluoroacetic acid was added thereto. The reaction was continued at room temperature for 6 h, and separated with a silica gel column, to give Compound 7—(25R)-3β-S-(6-aminohexanethioate)-spirost-5-ene (0.20 g, 72%) as a white solid.

$^1$H NMR (400 MHz, CDCl$_3$) δ 5.26 (s, 29H), 3.70-3.44 (m, 137H), 3.22 (s, 54H), 2.66 (s, 54H), 2.63 (s, 53H), 2.45 (s, 44H), 2.28 (d, J=1.3 Hz, 56H), 2.14 (s, 25H), 2.07 (s, 16H), 1.93 (s, 45H), 1.89 (d, J=1.9 Hz, 64H), 1.76 (s, 25H), 1.75 (d, J=6.0 Hz, 100H), 1.64 (s, 70H), 1.61-1.48 (m, 454H), 1.42 (s, 27H), 1.36-1.18 (m, 273H), 1.16 (d, J=19.0 Hz, 8H), 1.10 (s, 103H), 0.95 (s, 160H), 0.90 (s, 153H), 0.86 (s, 161H), 0.78 (d, J=17.5 Hz, 183H). (M+H$^+$)=544.3744.

Example 3

Preparation of (25R)-3β-N-(2-(tert-butoxycarbonyl)-amino-6-N-aminohexanoic acid methyl ester)-spirost-5-ene (8)

Compound 2—2-tert-butoxycarbonyl-amino-6-aminohexanoic acid methyl ester (2.6 g) and glacial acetic acid (0.2 ml) were dissolved in 50 ml of anhydrous 1,2-dichloroethane, and sodium cyanoborohydride (1.26 g) was added batchwise at room temperature. After reaction completion was detected by TLC, the reaction mixture was washed successively with a 5% sodium chloride solution, dilute hydrochloric acid and a saturated sodium bicarbonate solution, dried over anhydrous sodium sulfate, and separated with a silica gel column, to give Compound 8—(25R)-3β-N-(2-(tert-butoxycarbonyl)-amino-6-N-aminohexanoic acid methyl ester)-spirost-5-ene (3.49 g, 53.1%) as a white solid.

$^1$H NMR (400 MHz, CDCl$_3$) δ 5.27 (s, 1H), 4.60 (s, 2H), 4.51 (s, 1H), 4.17 (s, 2H), 3.58 (d, J=80.0 Hz, 8H), 3.25 (s, 2H), 2.57 (s, 2H), 2.28 (s, 1H), 2.19 (s, 1H), 2.03 (s, 1H), 1.96-1.82 (m, 10H), 1.80 (s, 2H), 1.74-1.62 (m, 9H), 1.61-1.51 (m, 10H), 1.49-1.38 (m, 27H), 1.36-1.22 (m, 11H), 1.20 (s, 2H), 0.94 (s, 6H), 0.90 (s, 6H), 0.86 (s, 6H), 0.80 (s, 6H), 0.71 (s, 1H). (M+H$^+$)=657.4765.

Preparation of (25R)-3β-N-(2-propyn-amino-6-N-aminohexanoic acid methyl ester)-spirost-5-ene (9)

Compound 8 (3.28 g) was dissolved in 50 ml of methylene chloride, and 5 ml of trifluoroacetic acid was slowly added dropwise at room temperature. Reaction completion was detected by TLC, and the intermediate (25R)-3β-N-(2-amino-6-N-aminohexane acid methyl ester)-spirost-5-ene was isolated with a silica gel column.

The above intermediate and potassium carbonate (276 mg) were dissolved in N,N-dimethylformamide, and propynyl bromide (0.5 ml) was added under water-ice cooling. After 30 min, the reaction was warmed to room temperature, and continued for 4 h. The solvent was removed under vacuum. The residue was dissolved in ethyl acetate, washed successively with a 5% sodium chloride solution, dilute hydrochloric acid and a saturated sodium bicarbonate solution, dried over anhydrous sodium sulfate, and separated with a silica gel column, to give Compound 9—(25R)-3β-N-(2-propyn-amino-6-N-aminohexanoic acid methyl ester)-spirost-5-ene (1.86 g, 62.3%) as a slightly yellow solid.

$^1$H NMR (400 MHz, CDCl$_3$) δ 5.26 (s, 1H), 4.30 (s, 2H), 3.65 (s, 5H), 3.49 (s, 2H), 3.38-3.22 (m, 5H), 3.16 (s, 1H), 3.07 (s, 2H), 2.56 (s, 3H), 2.32 (s, 1H), 2.18 (s, 1H), 2.11 (s, 3H), 2.06-1.96 (m, 5H), 1.94 (s, 1H), 1.87 (d, J=15.1 Hz, 3H), 1.80-1.73 (m, 8H), 1.69 (d, J=2.9 Hz, 3H), 1.64 (s, 2H), 1.55 (dd, J=22.8, 12.5 Hz, 7H), 1.50-1.38 (m, 8H), 1.38-1.15 (m, 12H), 1.38-0.96 (m, 13H), 1.38-0.82 (m, 30H), 1.38-0.74 (m, 36H). (M+H$^+$)=595.4398.

Preparation of (25S)-3β-N-(2-propyn-amino-6-N-aminohexanoic acid methyl ester)-furost-5-en-26-ol (10)

Compound 9 (1.79 g) was dissolved in 30 ml of a glacial acetic acid/methylene chloride (v:v=1:2) solution, and sodium cyanoborohydride (1.89 g) was added batchwise at room temperature. After reaction completion was detected by TLC, the reaction mixture was washed successively with a 5% sodium chloride solution, dilute hydrochloric acid and a saturated sodium bicarbonate solution, dried over anhydrous sodium sulfate, and separated with a silica gel column, to give Compound 10—(25S)-3β-N-(2-propyn-amino-6-N-aminohexanoic acid methyl ester)-furost-5-en-26-ol (1.23 g, 68.7%) as a white solid.

$^1$H NMR (400 MHz, CDCl$_3$) δ 5.27 (s, 1H), 3.70 (s, 1H), 3.66 (s, 7H), 3.53 (s, 2H), 3.47 (s, 3H), 3.31-3.21 (m, 6H), 3.08 (s, 2H), 2.85 (s, 1H), 2.57 (s, 3H), 2.34 (s, 1H), 2.24 (dd, J=22.0, 9.5 Hz, 1H), 2.19 (s, 3H), 2.29-1.96 (m, 11H), 2.29-1.91 (m, 14H), 2.29-1.87 (m, 16H), 2.29-1.80 (m, 19H), 2.29-0.91 (m, 81H), 1.48-1.38 (m, 11H), 1.52-0.91 (m, 45H), 1.37-1.22 (m, 19H), 0.92 (d, J=20.0 Hz, 14H), 0.88-0.80 (m, 12H), 0.79 (s, 3H). (M+H$^+$)=597.4554.

Preparation of (25S)-3β-N-(2-propyn-amino-6-N-aminohexanoic acid methyl ester)-26-O-(2,3,5-tri-O-acetyl-β-D-ribofuranosyl)-furost-5-ene (11)

Compound 10 (1.19 g) and 1,2,3,5-tetraacetyl-β-D-ribose (1.01 g) were dissolved in an anhydrous dichloromethane/acetonitrile solution. 0.3 ml of anhydrous Tin(IV) chloride was added dropwise under ice cooling. The reaction was stirred for 30 min, and then warmed to room temperature. After the reaction was completed, the reaction mixture was washed with a dilute sodium chloride solution, a dilute hydrochloric acid solution and a saturated sodium bicarbonate solution, dried over anhydrous sodium sulfate, and separated with a silica gel column, to give the compound (25S)-3β-N-(2-propyn-amino-6-N-aminohexanoic acid methyl ester)-26-O-(2,3,5-tri-O-acetyl-β-D-ribofuranosyl)-furost-5-ene (1.31 g, 71%) having a white color.

$^1$H NMR (400 MHz, CDCl$_3$) δ 5.55 (s, 2H), 5.46 (s, 3H), 5.24 (d, J=0.7 Hz, 5H), 4.93 (s, 2H), 4.83 (d, J=91.3 Hz, 5H), 3.86 (s, 3H), 3.81 (s, 3H), 3.64 (s, 10H), 3.49 (s, 2H), 3.40 (s, 3H), 3.28 (d, J=14.9 Hz, 8H), 3.13 (d, J=14.4 Hz, 5H), 3.06 (s, 4H), 2.55 (s, 5H), 2.32 (s, 2H), 2.18 (s, 1H), 2.05-1.96 (m, 40H), 1.93 (s, 2H), 1.88 (s, 4H), 1.83 (d, J=4.6 Hz, 6H), 1.81-1.72 (m, 13H), 1.65 (d, J=18.9 Hz, 5H), 1.57-1.47 (m, 12H), 1.46-1.39 (m, 11H), 1.32-1.21 (m, 21H), 1.13 (s, 2H), 1.09 (s, 4H), 1.11-0.74 (m, 47H). (M+H$^+$)=855.5297.

Preparation of (25S)-3β-N-(2-propyn-amino-6-N-aminohexanoic acid)-26-O-(2,3,5-tri-O-acetyl-β-D-ribofuranosyl)-furost-5-ene (12)

Compound 11 (1.07 g) was dissolved in 20 ml of a dichloromethane/methanol (v:v=1:1) mixture, and a 0.1 M sodium methoxide solution (0.5 ml) was added dropwise. The reaction was stirred for 4 h at room temperature, and 50 ml of methylene chloride was added. The reaction mixture was washed with a dilute sodium chloride solution, a dilute hydrochloric acid solution and a saturated sodium bicarbonate solution, dried over anhydrous sodium sulfate, and separated with a silica gel column, to give Compound 12—(25S)-3β-N-(2-propyn-amino-6-N-aminohexanoic acid)-26-O-(2,3,5-tri-O-acetyl-β-D-ribofuranosyl)-furost-5-ene (708 mg, 79.2%) having a white color.

$^1$H NMR (400 MHz, CDCl$_3$) δ 5.27 (s, 2H), 5.06 (s, 4H), 4.51 (s, 2H), 4.40 (s, 3H), 4.07 (s, 3H), 3.82 (s, 3H), 3.69 (s, 2H), 3.53 (s, 3H), 3.48 (s, 4H), 3.44 (s, 3H), 3.31 (d, J=14.8 Hz, 8H), 3.16 (s, 3H), 3.08 (s, 4H), 2.97 (s, 2H), 2.57 (s, 4H), 2.49 (s, 4H), 2.29 (s, 3H), 2.19 (s, 2H), 2.04 (d, J=7.8 Hz, 4H), 1.91 (t, J=12.5 Hz, 10H), 1.66 (q, J=3.1 Hz, 14H), 1.59-1.51 (m, 10H), 1.48-1.37 (m, 21H), 1.85-0.79 (m, 159H), 1.71-0.79 (m, 148H), 1.33-1.17 (m, 34H), 1.12 (d, J=17.9 Hz, 6H), 0.94 (s, 12H), 0.90 (s, 12H), 0.86 (s, 12H), 0.78 (d, J=19.1 Hz, 15H). (M+H$^+$)=715.4820.

Compound 13 was obtained in the same way as the preparation of Compound 10, using the compound 1,6-aminocaproic acid as the starting material.

(25S)-furost-5-en-3β,26-di-O-(6-aminohexanoate) (13)

$^1$H NMR (400 MHz, CDCl$_3$) δ 5.28 (s, 4H), 4.62 (s, 3H), 4.44 (s, 10H), 4.22 (d, J=33.8 Hz, 13H), 3.514 (s, 5H), 2.65 (s, 15H), 2.34 (d, J=15.0 Hz, 23H), 2.26 (s, 6H), 2.17 (d, J=3.4 Hz, 12H), 2.06 (s, 4H), 1.86 (dt, J=14.3, 8.8 Hz, 39H), 1.76 (s, 4H), 1.68-1.56 (m, 38H), 1.61 (t, J=11.0 Hz, 45H), 1.43 (d, J=19.9 Hz, 23H), 1.37-1.27 (m, 51H), 1.22 (d, J=6.4 Hz, 13H), 1.07 (s, 29H), 1.03 (s, 8H), 0.96-0.84 (m, 66H), 0.80 (s, 22H). (M+H$^+$)=643.4973.

Compound 14 was obtained using the compounds 4,6-aminocaproic acid and 3-deoxyribose as the starting materials:

(25S)-3β-N-(6-aminohexanoic acid)-26-O-(3-deoxy-β-D-ribofuranosyl)-furost-5-ene (14)

$^1$H NMR (400 MHz, CDCl$_3$) δ 5.28 (s, 13H), 4.88 (s, 24H), 4.53 (s, 9H), 4.49 (s, 21H), 4.38 (s, 24H), 4.14 (s, 14H), 3.53 (dd, J=100.4, 24.5 Hz, 88H), 3.38 (s, 5H), 3.13 (s, 24H), 2.70 (s, 24H), 2.40 (d, J=9.7 Hz, 52H), 2.20 (d, J=19.5 Hz, 35H), 2.18 (s, 20H), 2.02 (s, 12H), 1.82 (dd, J=16.9, 10.4 Hz, 69H), 1.83-1.75 (m, 77H), 1.72-1.62 (m, 81H), 1.54 (dd, J=22.7, 12.3 Hz, 134H), 1.42-1.27 (m, 175H), 1.28-1.18 (m, 77H), 1.08 (s, 46H), 0.96-0.84 (m, 211H), 0.81 (s, 73H). (M+H$^+$)=646.4606.

Example 4

Preparation of (25R)-3-O-benzyl-26-O-(tert-butyldimethylsilyl)-cholest-5-en-16β-ol (15)

Compound 1—(25R)-spirost-5-en-3β-ol (4.14 g) was dissolved in an anhydrous tetrahydrofuran/N,N-dimethylformamide (v:v=1:1) solution, and sodium hydride solid (0.5 g) was added. The reaction was warmed to 80-100° C. gradually. After the reaction was completed, the solvent was distilled off, and recrystallization from methanol offered Intermediate Compound 14a—(25R)-3-O-benzyl-spirost-5-en-3β-ol.

Intermediate Compound 14a was dissolved in a 10% concentrated hydrochloric acid-ethanol solution, and zinc powder (1.3 g) was added batchwise. The reaction was refluxed until the starting materials disappeared. The reaction mixture was filtered, and the filtrate was concentrated. The residue was recrystallized from ethanol-water, to give Intermediate Compound 14b—(25R)-3-O-benzyl-cholest-5-en-16β,26-diol.

Compound 14b was dissolved in N,N-dimethylformamide, and imidazole (0.7 g) and tert-butyldimethylsilyl chloride (1.7 g) were added under ice cooling. The reaction was stirred overnight, and the solvent was removed by rotary evaporation under a reduced pressure. The residue was dissolved in 50 ml of dichloromethane, washed three times with a 5% sodium chloride solution, dried over anhydrous sodium sulfate, and separated with a silica gel column (petroleum ether:ethyl acetate v:v=10:1, containing 0.5% triethylamine), to give the title compound (25R)-3-O-benzyl-26-O-(tert-butyldimethylsilyl)-cholest-5-en-16β-ol (3.24 g, total yield 53.4%).

$^1$H NMR (400 MHz, CDCl$_3$) δ 7.33 (d, J=5.0 Hz, 151H), 4.82 (s, 59H), 3.87 (d, J=22.3 Hz, 54H), 3.57 (d, J=0.9 Hz, 55H), 1.92 (d, J=17.9 Hz, 65H), 1.75 (d, J=8.7 Hz, 43H), 1.72-1.61 (m, 131H), 1.55 (s, 62H), 1.46 (s, 20H), 1.42 (d, J=13.3 Hz, 50H), 1.32-1.14 (m, 262H), 1.05 (s, 12H), 0.95 (d, J=9.2 Hz, 291H), 0.85 (d, J=10.0 Hz, 179H), 0.82 (s, 87H), 0.76 (s, 89H), 0.22 (s, 177H). (M+H$^+$)=599.4782.

Preparation of (25R)-3-O-benzyl-16-O-(2,3,5-tri-O-acetyl-β-D-ribofuranosyl)-cholest-5-en-26-ol (17)

Compound 15 (3.03 g) and 1,2,3,5-tetraacetyl-β-D-ribose (2.39 g) were dissolved in an anhydrous dichloromethane/acetonitrile solution. 0.5 ml of anhydrous Tin(IV) chloride was added dropwise under ice-water cooling. The reaction was stirred for 30 min, and then warmed to room temperature. After the reaction was completed, the reaction mixture was washed with a dilute sodium chloride solution, a dilute hydrochloric acid solution and a saturated sodium bicarbonate solution, and dried over anhydrous sodium sulfate. The organic phase was concentrated, and recrystallized from methanol, to give Intermediate Compound 16 (25R)-3-O-benzyl-16-O-(2,3,5-tri-O-acetyl-β-D-ribofuranosyl)-26-O-(tert-butyldimethylsilyl)-cholest-5-ene having a white color.

Intermediate Compound 16 was dissolved in tetrahydrofuran, and tetrabutylammonium fluoride (2.6 g) was added at room temperature. The reaction was stirred for 6 h, and the solvent was distilled off. The residue was dissolved in methylene chloride, and washed successively with a dilute sodium chloride solution, a dilute hydrochloric acid solution and a saturated sodium bicarbonate solution, dried over anhydrous sodium sulfate, and separated with a silica gel column, to give Compound 17—(25R)-3-O-benzyl-16-O-(2,3,5-tri-O-acetyl-β-D-ribofuranosyl)-cholest-5-en-26-ol (1.92 g, 50%) as a white solid.

$^1$H NMR (400 MHz, CDCl$_3$) δ 7.32 (d, J=5.0 Hz, 103H), 6.06 (s, 21H), 5.56 (s, 18H), 5.46 (s, 12H), 5.27 (s, 12H), 5.18 (s, 20H), 4.92 (s, 21H), 4.66 (s, 40H), 4.14 (s, 21H), 3.75 (d, J=42.8 Hz, 42H), 3.35 (s, 8H), 3.17 (s, 17H), 2.26 (s, 12H), 2.17 (s, 8H), 2.11 (s, 15H), 2.07-2.00 (m, 202H), 1.96 (s, 14H), 1.88 (d, J=11.5 Hz, 43H), 1.68 (t, J=17.5 Hz, 53H), 1.54 (t, J=8.0 Hz, 57H), 1.45 (s, 14H), 1.42-1.23 (m, 212H), 1.22 (s, 15H), 0.97-0.64 (m, 260H), 0.65 (d, J=3.1 Hz, 3H). (M+H$^+$)=767.4657.

Preparation of (25R)-3-O-benzyl-16-O-(2,3,5-tri-O-acetyl-β-D-ribofuranosyl)-26-(4-O-7-nitro-1,2,3-benzoxadiazol)-cholest-5-ene (18)

Compound 17 (1.53 g) and potassium carbonate (0.35 g) were dissolved in N,N-dimethylformamide, and 4-chloro-7-nitro-2,1,3-benzoxadiazole (0.5 g) was added at room temperature. The reaction was stirred for 2 h, and the solvent was evaporated to dryness. The residue was purified with a silica gel column to give Compound 18—(25R)-3-O-benzyl-16-O-(2,3,5-tri-O-acetyl-β-D-ribofuranosyl)-26-(4-O-7-nitro-1,2,3-benzoxadiazol)-cholest-5-ene (1.32 g, 71%) having a red brown color.

$^1$H NMR (400 MHz, CDCl$_3$) δ 8.15 (s, 19H), 7.32 (d, J=5.0 Hz, 93H), 6.94 (s, 19H), 5.57 (s, 18H), 5.52 (d, J=7.5 Hz, 37H), 5.25 (s, 10H), 5.16 (s, 18H), 4.71 (s, 36H), 4.47 (s, 13H), 4.39 (s, 22H), 4.08 (d, J=38.1 Hz, 38H), 3.76 (s, 19H), 3.39 (s, 7H), 2.48 (s, 23H), 2.23 (s, 11H), 2.15 (s, 10H), 2.12 (d, J=18.2 Hz, 40H), 2.08-2.00 (m, 183H), 1.94 (s, 23H), 1.91-1.82 (m, 46H), 1.71 (s, 9H), 1.64 (s, 16H), 1.55 (d, J=10.6 Hz, 32H), 1.50-1.44 (m, 33H), 1.35 (d, J=8.4 Hz, 37H), 1.34-1.21 (m, 116H), 0.94 (s, 55H), 0.88 (d, J=10.0 Hz, 111H), 0.82 (s, 58H). (M+H$^+$)=930.4677.

Preparation of (25R)-16-O-(2,3,5-tri-O-acetyl-β-D-ribofuranosyl)-26-(4-O-7-nitro-1,2,3-benzoxadiazol)-cholest-5-en-3-ol (19)

Compound 18 (0.93 g) was dissolved in ethyl acetate, and 30% Pd—C (0.5 g) was added. The reaction was stirred for 10 min, and hydrogen was bubbled in at 40° C. for 20 min. The reaction was continued for 1 h, filtered, and separated with a silica gel column, to give Compound 19—(25R)-16-O-(2,3,5-tri-O-acetyl-β-D-ribofuranosyl)-26-(4-O-7-nitro-1,2,3-benzoxadiazol)-cholest-5-en-3-ol (638 mg, 76%).

$^1$H NMR (400 MHz, CDCl$_3$) δ 8.14 (s, 47H), 6.85 (s, 47H), 5.57 (s, 47H), 5.53-5.47 (m, 91H), 5.25 (s, 26H), 5.18 (s, 46H), 4.63 (d, J=4.4 Hz, 12H), 4.54 (d, J=85.0 Hz, 75H), 4.09 (d, J=38.9 Hz, 95H), 3.82 (s, 37H), 3.45 (s, 18H), 2.28 (t, J=8.5 Hz, 13H), 2.26 (s, 59H), 2.38-2.06 (m, 194H), 2.37-1.92 (m, 745H), 1.88 (s, 32H), 1.83 (s, 29H), 1.72 (s, 23H), 1.65 (s, 71H), 1.59-1.52 (m, 86H), 1.49-1.37 (m, 114H), 1.37-1.19 (m, 441H), 0.96 (s, 138H), 0.88 (d, J=10.0 Hz, 274H), 0.82 (s, 145H). (M+H$^+$)=840.4205.

Preparation of (25R)-16-O-(2,3,5-tri-O-acetyl-β-D-ribofuranosyl)-26-(4-O-7-nitro-1,2,3-benzoxadiazol)-cholest-5-en-3-O-yl 2,6-diaminohexanoate (20)

Compound 19 (504 mg), N,N-2,6-di-tert-butoxycarbonyl-hexanoic acid (622 mg) and N,N-dimethylpyridine (24 mg) were dissolved in 20 ml of anhydrous dichloromethane. A solution of 1-ethyl-(3-dimethylaminopropyl)carbodiimide hydrochloride (460 mg) in 20 ml of anhydrous methylene chloride was added, and reacted for 6 h at room temperature. The reaction mixture was washed successively with a dilute sodium chloride solution, a dilute hydrochloric acid solution and a saturated sodium bicarbonate solution, dried over anhydrous sodium sulfate, and filtered. Trifluoroacetic acid (2 ml) was added to the filtrate, and reacted for 2 h at room temperature. The reaction mixture was washed successively with a dilute sodium chloride solution, a dilute hydrochloric acid solution and a saturated sodium bicarbonate solution, dried over anhydrous sodium sulfate, and separated with a silica gel column, to give Compound 20—(25R)-16-O-(2,3,5-tri-O-acetyl-β-D-ribofuranosyl)-26-(4-O-7-nitro-1,2,3-benzoxadiazol)-cholest-5-en-3-O-yl 2,6-diaminohexanoate (584 mg, 59%) as a brown solid.

$^1$H NMR (400 MHz, CDCl$_3$) δ 8.18 (s, 4H), 6.82 (s, 4H), 5.56 (d, J=4.4 Hz, 6H), 5.46 (s, 4H), 5.34 (s, 4H), 5.27 (s, 2H), 4.35 (s, 2H), 4.22 (d, J=10.6 Hz, 9H), 4.15 (s, 2H), 4.06 (s, 3H), 3.76 (s, 3H), 3.35 (s, 2H), 2.67 (s, 5H), 2.58 (s, 3H), 2.36 (s, 2H), 2.17 (d, J=3.0 Hz, 5H), 2.14 (s, 5H), 2.05-1.92 (m, 54H), 1.85 (d, J=17.4 Hz, 10H), 1.83 (s, 5H), 1.73 (d, J=4.2 Hz, 4H), 1.68-1.56 (m, 15H), 1.55 (s, 4H), 1.47 (d, J=8.5 Hz, 11H), 1.37 (s, 2H), 1.36-1.21 (m, 40H), 0.96 (s, 12H), 0.89 (d, J=10.0 Hz, 23H), 0.83 (s, 14H), 0.66 (s, 2H). (M+H$^+$)=968.5155.

I claim:
1. A compound of the formula:

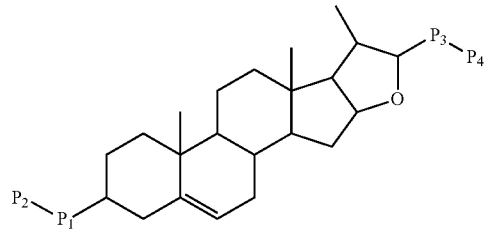

or a pharmaceutically acceptable salt thereof,
wherein
$P_1$ is selected from the group consisting of N, S, and $C_1$-$C_8$ hydrocarbyl;
$P_2$ is selected from the group consisting of $C_6H_5CO$, $R_3NH(CH_2)_nCO$, $R_5NHCH(R_4)CO$, sulfonyl, diethoxyphosphonate, 2-[bis(pivaloyloxy)methoxy]phosphonomethoxyethyl, glucosyl, galactosyl, ribosyl, deoxyribosyl, rhamnosyl, arabinosyl, lactosyl, and a group according to the formula -$A_1A_2$;
$P_3$ is selected from the group consisting of O, N, S, and $C_1$-$C_8$ hydrocarbyl;
$P_4$ is selected from the group consisting of $CH_3CO$, $C_6H_5CO$, $R_3NH(CH_2)_nCO$, $R_5NHCH(R_4)CO$, sulfonyl, diethoxyphosphonate, 2-[bis(pivaloyloxy)methoxy]phosphonomethoxyethyl, glucosyl, galactosyl, ribosyl, deoxyribosyl, rhamnosyl, arabinosyl, lactosyl, and a group according to the formula -$A_1A_2$;
$R_3$ and $R_5$ are independently selected from the group consisting of H, $CH_3CO$, $C_6H_5CO$, sulfonyl, diethoxyphosphonate, a saturated or unsaturated $C_1$-$C_{18}$ hydrocarbyl group, and a heterocyclic group;
$R_4$ is selected from the group consisting of a saturated or unsaturated $C_1$-$C_{18}$ hydrocarbyl group, and a heterocyclic group;

n is 5; and

A$_1$ and A$_2$ are selected from the group consisting of hydrogen, a substituted or unsubstituted C$_1$-C$_{18}$ hydrocarbyl group, C$_3$-C$_{12}$ heterocyclyl, a substituted or unsubstituted C$_1$-C$_{18}$ aliphatic acid group, a C$_1$-C$_{18}$ alkyl group substituted by C$_3$-C$_{12}$ heterocyclyl; and an aliphatic acid group substituted by C$_3$-C$_{12}$ heterocyclyl.

2. A compound which is (25S)-furost-5-en-3β,26-di-O-(6-aminohexanoate).

3. The compound of claim 1, wherein:

P$_2$ is selected from the group consisting of C$_6$H$_5$CO, R$_3$NH(CH$_2$)$_n$CO, R$_5$NHCH(R$_4$)CO, sulfonyl, diethoxyphosphonate, 2-[bis(pivaloyloxy)methoxy]phosphonomethoxyethyl, glucosyl, galactosyl, ribosyl, deoxyribosyl, rhamnosyl, arabinosyl, and lactosyl; and P$_4$ is selected from the group consisting of CH$_3$CO, C$_6$H$_5$CO, R$_3$NH(CH$_2$)$_n$CO, R$_5$NHCH(R$_4$)CO, sulfonyl, diethoxyphosphonate, 2-[bis(pivaloyloxy)methoxy]phosphonomethoxyethyl, glucosyl, galactosyl, ribosyl, deoxyribosyl, rhamnosyl, arabinosyl, and lactosyl.

\* \* \* \* \*